United States Patent [19]

Rodriguez

[11] Patent Number: 5,295,494
[45] Date of Patent: Mar. 22, 1994

[54] SUPPORT FOR A THERAPEUTIC MAGNET

[76] Inventor: Andres C. Rodriguez, Parque Residencial Nuestra senora de la Merced, Bloque 5-3°-C, 11406 Jerez de la Frontera, Cadiz, Spain

[21] Appl. No.: 883,649

[22] Filed: May 15, 1992

[30] Foreign Application Priority Data

May 17, 1991 [ES] Spain .................... 9101529

[51] Int. Cl.$^5$ .................... A61G 15/00; A61B 17/52
[52] U.S. Cl. .................... 128/845; 600/9; 206/818
[58] Field of Search .................... 128/874, 875, 876, 845; 220/230; 206/818; 600/9

[56] References Cited

U.S. PATENT DOCUMENTS

| 712,447 | 10/1902 | Woolley | 220/230 |
| 754,386 | 3/1904 | Norris | 128/100.1 |
| 2,272,444 | 2/1942 | Testi | 206/818 |
| 3,141,258 | 7/1964 | Mayer | 206/818 |
| 3,763,996 | 10/1973 | Shepherd | 206/818 |
| 4,577,750 | 3/1986 | Bennardo | 220/230 |
| 4,660,715 | 4/1987 | Anastos | 206/818 |
| 4,727,984 | 3/1988 | Bennardo | 220/230 |

OTHER PUBLICATIONS

Dr. H. L. Bansal, *Magnetic Cure For Common Diseases*, Second Revised Edition, B. Jain Publishers, New Delhi.
Dr. M. T. Santwani, *Magnetotherapy for Common Diseases*, First Edition, 1981, B. Jain Publishers, New Delhi.
*Davis, A. R. et al., *Magnets and Magnetic Fields or Healing by Magnets*, K. L. Mukhopadhyay, Bancharan Akrur, Lane Calcutta.
*Bansal, H. L., *Mangetotheraphy*, Second Revised Edition, B. Jain Publishers, New Delhi.
*Barbieri, M., et al., *Sensibilita delle Cellule Coltivate in Vitro All'azione del Campo Magnetico*, Atti Acc. Naz. Lincei, 49, 153-161, 1970.
*Barnothy, M. F., *Biological Effects of Magnetic Fields*, Plenum Press, N.Y., vol. I, 1964, vol. II, 1969.
*Beischer, D. E., *Human Tolerance to Magnetic Fields*, Aeronautics, Mar. 25, 1962.
*Bergier, J., *L'Extraordinaire Decouverte de Piccardi*, Revue Planete, 5, pp. 83-87.
*Bondi, C., et al., *Su Alcune Rilevanti Alterazioni Morfologiche in Embrioni di Bufo e Rana Indotte da un Campo Magnetico Puntiforme*, Rivista di Biiologia, 72, 91-101, 1979.
*Bhattacharya, A. K., *Magnet Dowsing*, Second Edition, 1976, firma KLM Private Ltd., Calcutta.
*Brown, F. A., et al., *Magnetic Induction of a Circadian Cycle in Hamster*, J. Interdiscipl. Cycli, Res., 9, 137-145, 1978.
*Brown, Wenbb y Brett, *Magnetic Response of an Organism and its Lunar Relationship*, Biologic Bulletin, 1960, 18, No. 3, pp. 382-392.
*Budinger, T. G., *Nuclear Magnetic Resonance (NMR) in Vivo Studies: Know Threshold for Health Effects*, J. Comput. Assist. Tomogr. 800-811, 1981.

(List continued on next page.)

*Primary Examiner*—Michael A. Brown
*Attorney, Agent, or Firm*—Ostrolenk, Faber, Gerb & Soffen

[57] ABSTRACT

A support for a therapeutical magnet formed by a receptacle having the same cross-section as that of a box containing a magnet. The box is formed by two open inverted and facing halves. A coupling between the two halves at the edges thereof. The two halves are stopped by an edging depression made in one of the two halves in which the end of the wall of the other half is coupled. The base of one half of the two halves of the box has a central hollow in which is attached and fixed a transparent sheet of the same thickness as the hollow. Attached to the lower face of the transparent sheet is a printed film, containing information text, covered by an adhesive film on both faces, one of which attaches to the bottom of the hollow and the other to the lower face of the transparent sheet. The base of the support has a passage with two holes through which passes a belt that moves freely through these holes. The belt has a buckle on one end and also a device to adjust and hold the belt to the part of the body to which the magnet is to be applied.

15 Claims, 1 Drawing Sheet

OTHER PUBLICATIONS

*Cook, E. S., et al., *Biological Effects of Magnetic Fields. vol. I, Increase of Trypsin Activity*, Barnothy M. F., Editor, pp. 246–254, Plenum Press, New York, 1964.

*Council of Scientific and Industrial Research, *Magnetics Fields of Human Body*, Science Reporter, Jun. 1977, New Delhi.

*Cherbit, G., *Alternation of the Membrane Permeability Caused by a Pulsed Electromagnetic Field*, Inter. Symposium On Wave Therapeutics, Versatilles, 19–20, Mar. 1979, p. 18.

*Dantu P. et al., *Multiplication des Bacteries et des Bacteriophagues dans un Champ Magnetique*, Annales de L'Institute Pasteur, 112, 645, 196.

*Baron, J. B. et al., *Biomagnetisme et Orthopedie, et Nouvelle Therapeutique des Entorses et des Chevilles: Effectes des Champs Magnetiques*, Symposium International Danse et Medecine, Paris, Sorbonne, 1983.

*Bolakani, H. T., *Secrets of Magnetotherapy, the Acknowledge Science of Natural Healing and Cure*, (Bombay) Abstract of Biomagnetic Symposium, Japan (Aimante Mfg. Co. Tokyo, Japan). Clinical Effects of Magnetic Health Bands on the so called "Stiff Shoulders" (Tabata National Railway Hospital, Japan).

*Donnet, L., *Les Aimants pour Votre Sante*, Editions Dangles, 1985.

*Duval, C., *L'Eau, P.U.F.*, Paris, 1962, (IEEE) Trans. Magnetics, MAG-6, (1970), 321.

*Freeman, M. W., et al., *Magnetism in Medicine*, J. Appl. Phys. 31S (1960) 404.

*Friedman, H., *Effects of Magnetic field on Reaction Time Performance*, Nature, 213, 949–950, 1963.

*Friedman, H., et al., *Geomagnetic Parameters and Psychiatric Hospital Admissions*, Nature, 200, 626–628, 1963.

*Geacintov, N. E., *Magnetic field Effects on Biological Systems. Orientation of Biological Membranes and Cell in Magnetic Field*, T. Tenforde Editor, Plenum Press, New York, 1979, pp. 46–48.

*Gerencser, F. V., et al., *Inhibition of Bacterial Growth by Magentic Fields*, Nature, 213, 72, 1967.

*Haberditzl, W., *Physique sous Champs Magnetiques Intenses, Kinetic Effects in Magnetic Fields*, Colloques International du CNRS, No. 242, pp. 63–65, Grenoble, 1974.

*Haberditzl, W., *Enzyme Activity in Hight Magnetic Fields*, Nature, 213, 72, 1967.

*Hong, F. T., *Magnetic Field Effects of Biological Systems, Mechanism of Magnetic Field Interactions with Retinal Rods*, T. Tenforde, Editor, Plenum Press, New York, 1979, pp. 43–45.

*Kartsev, V. P., *Three Thousand Years of Magnets*, M. I. R. Pubulishers, Moscou.

*Kolin, A., *Magnetic Field in Biology*, Physics Today, 21, 39–50, 1968.

*Lenzi, M., *Prospettive Future degli Sutudi sugli Afetti Biologici e Clinici dei Campi Elecromagneti*, Relazione al I Congreso Internaionale di Medicina, Rapallo Oct. 28–29, 1979, Atti Ed. Minerva Medica, Torino, 1980.

*Mahlum, D. P., *Magnetic field Effects on Biological Systems, Mechanisma of biomagnetic Effects*, T. Tenforde Editor, Plenum Press, New York and London, 1979, pp. 83–84.

*Mizushima Y. et al., *Effects of Magnetic Fields on Inflammation*, Experientia. 31, 1411–1412, 1975.

*Neischer, D. E., *Biological Effects of Magnetic Fields*, Abstr. Aeropace Med., 32, 220, 1961.

*Neurath, P. W., *Biological Effects of Magnetic Fields*, II, New York, Plenum Press, 1969, 177.

*Pressman, A. S., *Electromagnetic Fields and Life*, Consulta's Bureau, Plenum Press, IFI/Plenum, Translated from Russian to English.

*Reno, V., et al., *Effects of magnetic Fields on Tissue Respiration*, Nature, 198, 204–205, 1963.

*Santwani, M. T., *The Art of Magnetic Healing*, First Edition, 1981, B. Jain Publishers, New Delhi.

*The Library of Congress, *Science and Technology Projections: Projects Magnetism and its Effects on Living Matter*, Prepared for the Office of Naval Research under contract Naor-13-47, Waashington, Mar. 1949.

*Union of Soviet Socialest Republics, *Magnetic Water*, Soviet Lan, No. 20, Oct., 1973.

*Volkov, E. I., *Magnetics in Living Organism*, Usp. Fiz. Nauk, 131, 719–720, 1980.

*Weissbluth, M., *Magnetic Fields Effects on Biological Systems, Enzyme-substrate Reactions in High Magnetic Fields*, T. Tenforde Editor, Plenum Press, New York and London, 1979, pp. 48–50.

U.S. Patent    Mar. 22, 1994    5,295,494
FIG.1
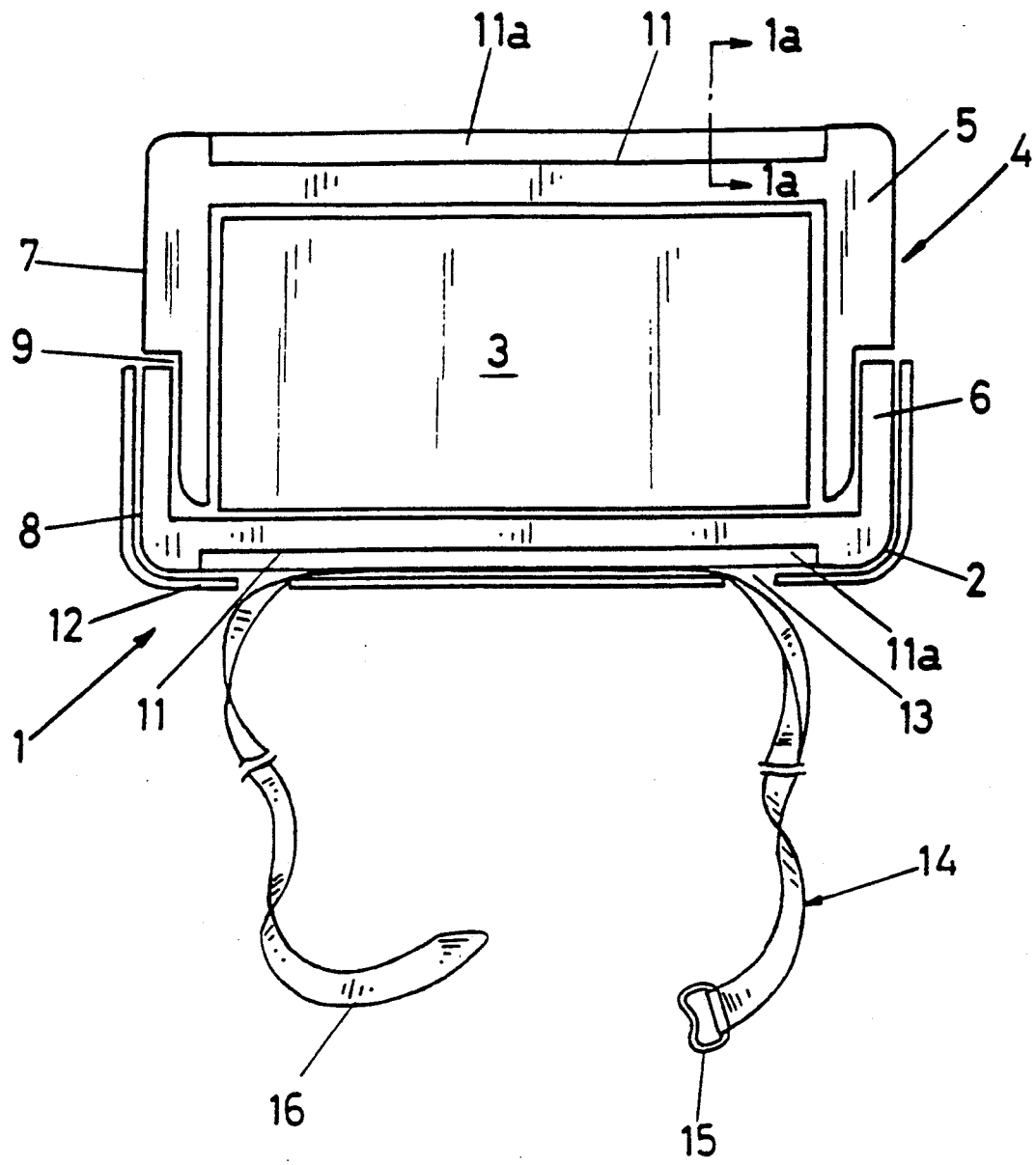
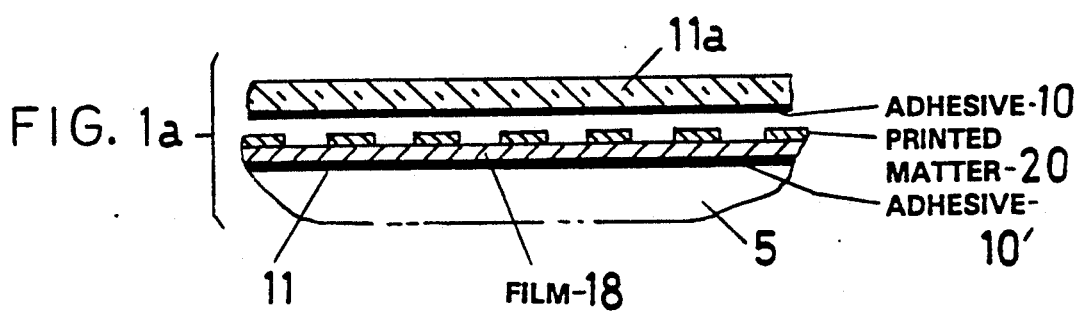
FIG. 1a

SUPPORT FOR A THERAPEUTIC MAGNET

BACKGROUND OF THE INVENTION

The present invention relates to a support for a therapeutic magnet.

As is well known, it has been proved that a magnetic field influences the human body. The cellular activity of the human body is influenced by an acceleration in the cellular changes because of the extra-cellular medium such as a magnetic field, which gives rise to the reconstitution of the electrical charge of the cellular membrane. Accordingly, the magnetic field exercises an influence on the permeability of sodium and potassium ions through the membranes, thus modifying the degree of excitability of the nerve and muscle tissue.

Moreover, at the level of transmission of nervous influxes, the influence of the magnetic field favors or inhibits the liberation of small quantities of neurotransmitters. At the level of cutaneous recovery, a staminic effect shows the action of the magnetic field on the autonomous nervous system by stimulation of the parasympathetic system. At the intracellular level, oxidative processes of mitochondria are increased by a greater consumption of oxygen. These findings are in agreement with known data on the physiology of pain that is usually accompanied by an oxygen deficiency at the tissue level.

The increase in local temperature caused by a magnetic field on a living tissue presumes an increase in blood circulation and the supply of oxygen to the zone.

It is also well known that the application of a static magnetic field to the human body has an unquestionable curative and improving action. The harmless nature of the magnetic field has also been demonstrated.

Aside from the therapeutical effects, numerous patients in various studies have indicated a general sensation of improvement in their health, and a decrease in the sensation of fatigue, as a result of the application of a magnet to the body. Therefore, magnets alleviate some illnesses and without any doubt have a positive effect on the general state of the person.

SUMMARY OF THE INVENTION

It is an object of the present invention to provide a support which has a novel construction and allows a preferably ring shaped magnet to be provided inside a receptacle or box with a cover that is placed on it.

Moreover, the support has means for coupling and attaching the support to a part of the human body, for example, an arm, leg, the head, etc., and for removing the support therefrom.

Accordingly, the present invention provides a support for a therapeutical magnet characterized in that it is formed by a receptacle of the same cross-section as that of a box containing a magnet. The box is formed by two inverted and facing halves, with the two halves having a coupling at the edge and being stopped by means of an edging depression made in one of the two halves in which the end of the wall of the other half is coupled. On the base of one half of the box is a central hollow in which is attached and fixed a transparent sheet of the same thickness as the hollow, and attached to the lower face of the sheet is a printed film with an information text covered by an adhesive film on both faces. One face of the printed film is attached to the bottom of the hollow and the other face to the lower face of the transparent sheet. On the base of the support are two holes through which is passed a band that moves freely through these holes with a buckle on one end of the belt, and also means to adjust and hold the belt to the part of the body to which the magnet is to be applied.

In order to more easily understand not only the formation but also the use of the support of the invention, reference is made below to a practical example, with this example being merely illustrative and in no case limiting the invention, with reference to the attached drawing.

BRIEF DESCRIPTION OF THE DRAWING

FIG. 1 is a schematic view of the support according to an embodiment of the present invention; and FIG. 1a is an exploded view along lines 1a-1a of FIG. 1.

DETAILED DESCRIPTION OF A PREFERRED EMBODIMENT OF THE INVENTION

FIG. 1 shows a support 1 formed by a receptacle 2. The magnet 3 is placed inside a box 4 made up of two inverted halves 5 and 6. The bases of the inverted halves 5 and 6 form opposing ends of the box 4.

One of these halves 5 has a lateral surface 7 of greater thickness than a lateral surface 8 of the other half 6 which is set against it. The lateral surface 7 has an external depression 9 which is formed around the edge thereof, and has a width substantially the same as the width of the lateral surface 8. A male/female coupling and a stop is thereby formed thereof, thus giving a perfect join between the two halves 5, 6 of the box 4.

The upper and lower ends of the box 4 each have a hollowed central zone 11, surrounding a central hollow in which is placed a transparent sheet 11a. FIG. 1a is an exploded view along lines 1a-1a of FIG. 1. On the lower face the transparent sheet 11a is attached a serigraph film (18) that holds text 20 with information. The serigraph film 18 is covered with an adhesive film 10, 10') on both sides; ine side of the film 18 being stuck to the transparent sheet 11a and the other side of the film 18 being stuck to the lower wall of the central hollow.

The support 1 has on its base 12 two holes 13 through which passes the band 14 with a ring 15 on one of its ends. The other end of the band 14 passes through the ring 15, and regulates the adjustment of the band 14 on the part of the body (not shown) on which it is desired to apply the magnet 3. The support 1 is attached by means of removable attachments 16 on the band 14 itself.

Having sufficiently described the nature of the invention and the way of putting it into practice, it must be noted that the above layouts indicated and represented in the attached drawings may be modified in their details, providing this does not alter the basic principle.

I claim:

1. A support for a therapeutic magnet, the support comprising:
   a box with an interior for containing the magnet, the box being comprised of two open, inverted and facing box parts, the box parts each having respective sets of upstanding walls; a stop in one of the sets of upstanding walls for defining a stopping position for the two parts with respect to each other; a coupling arrangement between the box parts at the edges thereof for releasably joining the two box parts together;

each box part having a base, at least one of the box part bases having a central hollow region defined therein on a side away from the interior of the box;

a transparent sheet having the same thickness as the hollow region being attached in the hollow region, the sheet having a bottom face on a side facing the interior of the box;

a printed film with information text on it applied to the bottom face of the sheet so that the information text is readable by a user of the support, the printed film having two opposite surfaces; the printed film having adhesive on both the surface toward the box interior and the surface toward the transparent sheet for attaching the printed film to respective opposing surfaces of the box and the transparent sheet, the printed film being between the hollow region in the respective box part and the bottom face of the transparent sheet; and a passage through one of the box parts; a band passing through the passage; and means for fastening the band to a part of a body to which the support and a magnet therein is to be applied.

2. The support of claim 1, wherein each box part is comprised of a respective box half, the box part having the stop in the associated upstanding walls also has the transparent sheet in the associated hollow region; and the other box part having the passage for the band formed therethrough.

3. The support of claim 1, wherein both box parts have respective central hollow regions defined therein on a side away from the interior of the box.

4. The support of claim 1, wherein the box part having the passage therethrough has respective spaced apart holes defining said passage, opposite end portions of the band passing freely through the spaced apart holes; means being provided to adjust the length of the band to hold the support and the magnet to the part of the body.

5. The support of claim 1, wherein the step comprises an edge depression formed in one of the sets of upstanding walls of the box parts; the edge depression stopping the ends of the other of the sets of upstanding walls.

6. The support of claim 1, wherein the transparent sheet and the printed film are on the base of one box part and the band on the base of the other box part.

7. The support of claim 1, wherein the box contains a magnet.

8. The support of claim 7, wherein the magnet is ring shaped.

9. A support for a therapeutic magnet, the support comprising:

a box with an interior for containing the magnet, the box being comprised of two open, facing box parts, the box parts each having respective sets of upstanding walls; a stop in one of the sets of upstanding walls for defining a stopping position for the two parts with respect to each other; a coupling between the box parts at the edge thereof;

each box part having a base, at least one of the box part bases having a central hollow region defined therein on a side away from the interior of the box;

text-displaying means disposed in the hollow region for providing information text readable by a user of the support; and a passage through one of the box parts; a band passing through the passage; and means for fastening the band to a part of a body to which the support and a magnet therein are to be applied.

10. The support of claim 9, wherein the text-displaying means comprises a transparent sheet disposed in the hollow region, the sheet having a bottom face on a side facing the interior of the box; and text-carrying means disposed between the hollow region in the respective box part and the bottom face of the transparent sheet.

11. The support of claim 10, wherein the transparent sheet and the text-carrying means are on the base of one box part and the band is at the base of the other box part.

12. The support of claim 9, wherein each box part is comprised of a respective box half.

13. The support of claim 9, wherein both box parts have respective central hollow regions defined therein on a side away from the interior of the box.

14. The support of claim 9, wherein the box part having the passage therethrough has respective spaced apart holes, opposite end portions of the band passing freely through the spaced apart holes; means being provided to adjust the length of the band to hold the support and the magnet to a body.

15. The support of claim 9, wherein the stop comprises an edge depression formed in one of the sets of upstanding walls of the box parts; the edge depression stopping the ends of the other of the sets of upstanding walls.

* * * * *